(12) United States Patent
Govyadinov et al.

(10) Patent No.: US 12,337,317 B2
(45) Date of Patent: Jun. 24, 2025

(54) CELL PORATION AND TRANSFECTION APPARATUSES

(71) Applicant: Hewlett-Packard Development Company, L.P., Spring, TX (US)

(72) Inventors: Alexander Govyadinov, Corvallis, OR (US); Viktor Shkolnikov, Palo Alto, CA (US); Diane R. Hammerstad, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 506 days.

(21) Appl. No.: 17/416,565

(22) PCT Filed: Jul. 25, 2019

(86) PCT No.: PCT/US2019/043393
§ 371 (c)(1),
(2) Date: Jun. 21, 2021

(87) PCT Pub. No.: WO2021/015779
PCT Pub. Date: Jan. 28, 2021

(65) Prior Publication Data
US 2022/0184610 A1    Jun. 16, 2022

(51) Int. Cl.
*B01L 3/00* (2006.01)

(52) U.S. Cl.
CPC ..... *B01L 3/50273* (2013.01); *B01L 3/502715* (2013.01); *B01L 2200/16* (2013.01); *B01L 2300/1833* (2013.01); *B01L 2400/0433* (2013.01); *B01L 2400/0478* (2013.01)

(58) Field of Classification Search
CPC .......... B01L 3/50273; B01L 3/502715; B01L 2200/16; B01L 2300/1833; B01L 2400/0433; B01L 2400/0478; C12M 35/04; C12M 35/00; C12N 15/87
See application file for complete search history.

(56) References Cited

U.S. PATENT DOCUMENTS 6,387,671 B1    5/2002  Rubinsky et al.
6,645,757 B1 *  11/2003 Okandan ................ C12M 35/02
                                                  204/403.01

(Continued)

FOREIGN PATENT DOCUMENTS

EP          1196549 B1    4/2010
WO    WO-2006112870 A1   10/2006

(Continued)

OTHER PUBLICATIONS

Khine, M. et al., "Single-cell electroporation arrays with real-time monitoring and feedback control", Mar. 7, 2007, Lab on a Chip, pp. 457-462.

*Primary Examiner* — P. Kathryn Wright
*Assistant Examiner* — Curtis A Thompson
(74) *Attorney, Agent, or Firm* — Foley & Lardner LLP (57) ABSTRACT

In example implementations, an apparatus is provided. The apparatus includes a channel, an energy source, and a transfection chamber. The channel includes an indentation to hold a cell. The energy source is to apply a shockwave to the cell in the channel to porate the cell. The transfection chamber is to store a reagent to be inserted into the cell after the cell is porated.

7 Claims, 7 Drawing Sheets

(56) References Cited

U.S. PATENT DOCUMENTS

| | | | |
|---|---|---|---|
| 6,743,779 B1 * | 6/2004 | Unger | A61K 9/127 |
| | | | 435/325 |
| 2002/0127144 A1 * | 9/2002 | Mehta | G01N 15/1031 |
| | | | 436/164 |
| 2006/0028908 A1 * | 2/2006 | Suriadi | F16K 99/0057 |
| | | | 366/146 |
| 2008/0138876 A1 * | 6/2008 | Ragsdale | C12M 35/02 |
| | | | 435/283.1 |
| 2011/0181668 A1 * | 7/2011 | Yang | B41J 2/14233 |
| | | | 29/890.1 |
| 2011/0213288 A1 | 9/2011 | Choi et al. | |
| 2012/0264134 A1 | 10/2012 | Ionescu-Zanetti et al. | |
| 2014/0273229 A1 * | 9/2014 | Meacham | C12M 35/04 |
| | | | 435/173.6 |
| 2015/0044751 A1 | 2/2015 | Chiou et al. | |
| 2015/0299730 A1 * | 10/2015 | Xu | C12N 15/87 |
| | | | 506/40 |
| 2018/0258379 A1 | 9/2018 | Zahn et al. | |
| 2021/0179991 A1 * | 6/2021 | Shkolnikov | C12N 15/87 |

FOREIGN PATENT DOCUMENTS

| | | | | |
|---|---|---|---|---|
| WO | WO-2009067142 A1 | | 5/2009 | |
| WO | WO-2017184178 A1 | | 10/2017 | |
| WO | WO-2018226240 A1 | * | 12/2018 | B01L 3/0268 |
| WO | WO-2019046304 A1 | | 3/2019 | |

\* cited by examiner

CELL PORATION AND TRANSFECTION APPARATUSES

BACKGROUND

Cell transfection may be used for research and production of certain biological products, such as synthetic proteins, genetically modified organisms, and the like. Cell transfection includes creating pores in a cell membrane of a cell and inserting a foreign material into the cell.

DETAILED DESCRIPTION

Examples described herein provide a system and apparatus for poration of cells for transfection. As noted above, transfection of cells can be used for research or production of certain biological products. Transfection allows the behavior of the cell to be changed. For example, by diffusing a reagent, such as a particular DNA along with proteins that incorporate the DNA into a cell's genome, the cell's genome may be altered to create a genetically modified organism.

Some systems to perform the poration and transfection can potentially introduce contamination. Some methods for poration use expensive tooling or may not provide sufficient control of the amount of material that is transfected into a cell. Other methods may also not allow for transfection with microscopic amounts of fluids in single cells.

Examples herein provide a system and apparatus for poration of cells for transfection. The apparatus may apply a shockwave energy to porate the cell. The shockwave energy may be provided by an energy source such as a TIJ resistor or a piezoelectric device. The design of the present apparatus can perform poration and transfection of cells without contamination. In addition, the energy source allows for single cell precision, which may provide better transfection yield and better survivability.

In one example, the system may also provide cell monitoring and a feedback control loop. For example, sensors may be implemented to detect the presence of a cell to control operation of the energy source. As a result, the energy source may be activated and deactivated based on whether cells are present in the apparatus.

In addition, the feedback control loop may detect if the cells have been porated for transfection. If not, the cells may be returned to the porating chamber to repeat the poration process. Thus, the system may ensure that the cells are properly porated.

Figure 1:
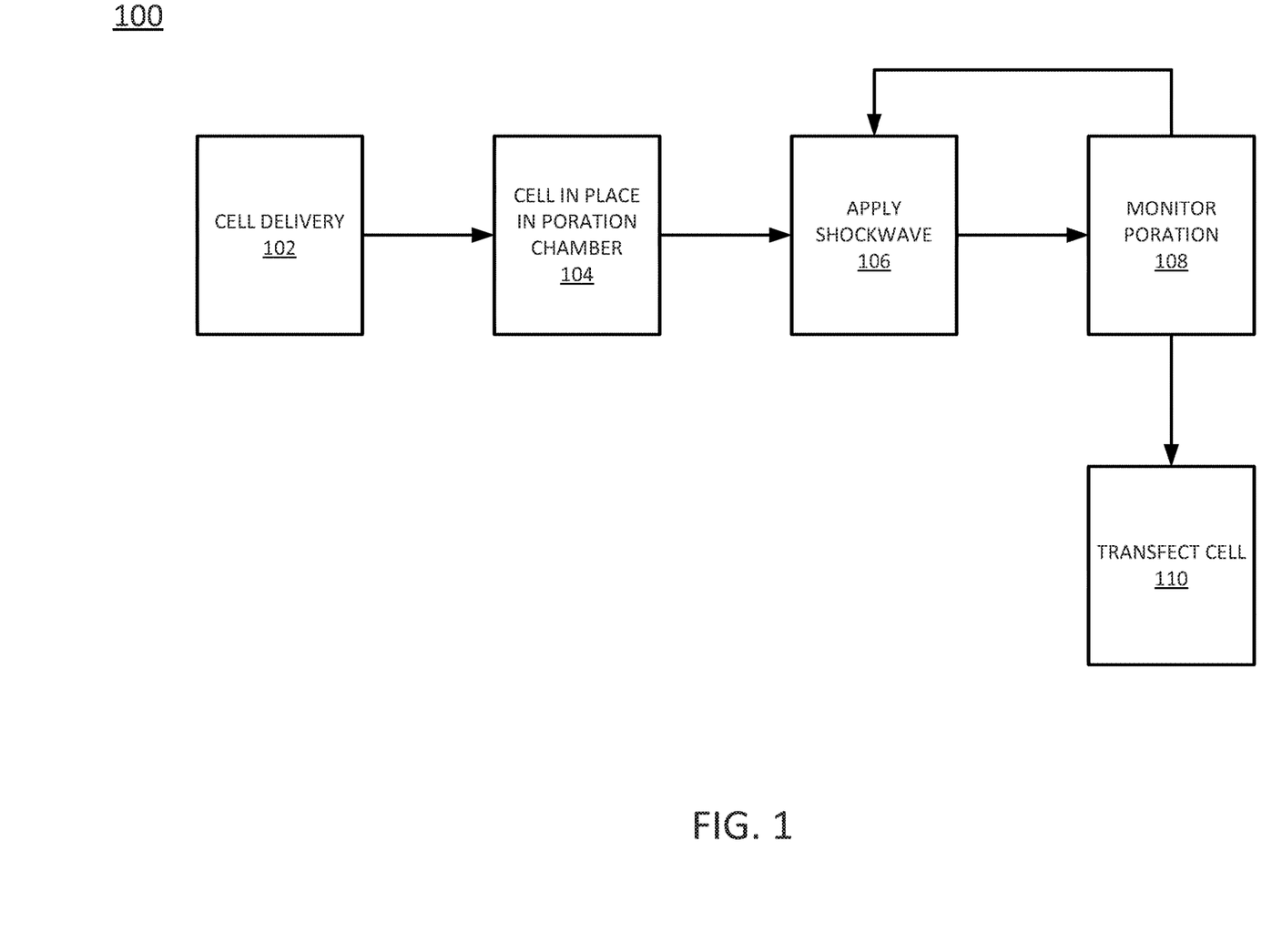
FIG. 1 is a block diagram of an example system to provide cell poration and transfection of the present disclosure.

FIG. 1 illustrates an example block diagram of a system 100 of the present disclosure. The block diagram of the system 100 provides an overview of how the apparatus described herein may operate. Different examples of the structure to perform the functions of each block of the system 100 are illustrated and discussed in further details below.

At block 102 cell delivery may be provided. For example, the cells may be stored in a reservoir in a fluid. The cells may be delivered via a pump. At block 104, the cells may be placed in a poration chamber and positioned to receive a shockwave or energy.

At block 106, the shockwave may be applied to the cell to porate the cell. The shockwave may create pores in the membrane of the cell. The pores may allow the cell to be transfected with a reagent. At block 108, the poration of the cell may be monitored. For example, a monitoring system may monitor whether or not pores are being properly formed in the cell. Based on the monitoring, the amount of shockwave that is applied to the cell can be adjusted as part of a feedback loop. As discussed in further details below, the amount of shockwave may be adjusted by adjusting an amplitude of the shockwave, adjusting a frequency of the shockwave, adjusting an amount of time the shockwave is applied, and the like.

If the cell is successfully porated, the cell may be released into a transfection chamber. At block 110, the cell may be transfected with a reagent. The reagent may be any type of molecule that can be injected into the cell. The type of reagent may be a function of a purpose of the transfection. For example, the reagent may be used to reprogram the cell, mutate the cell, or create new cells. The reagent may include DNA, RNA, proteins, nanoparticles, and the like.

Figure 2:
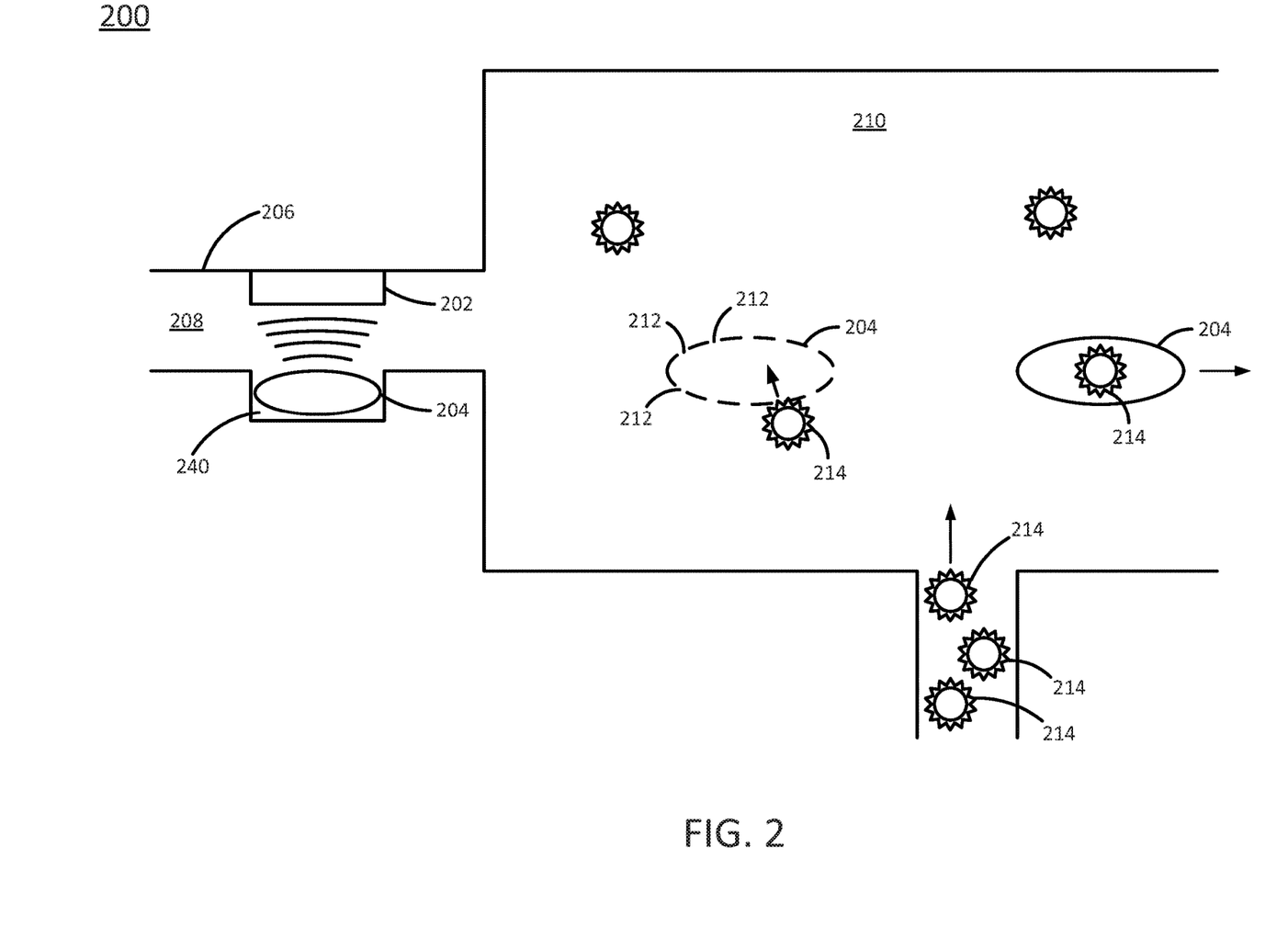
FIG. 2 is a block diagram of a cross-sectional view of an apparatus with an energy source to provide shockwave cell poration and transfection of the present disclosure.

FIG. 2 illustrates a block diagram of a cross-sectional view of an apparatus 200 with an energy source 202 to provide shockwave cell poration and transfection of the present disclosure. In one example, the apparatus 200 may include a poration chamber 206. A cell 204 may be provided through a channel 208 in the poration chamber 206. In one example, the channel 208 may include an indentation 240 to hold the cell 204. The indentation 240 may be a hole, a groove, an area, or the like, that is below a bottom surface of the channel 208. Thus, the cell 204 may temporarily "fall into" the indentation 240 to receive the shockwave.

In one example, the energy source 202 may be a TIJ resistor or a piezoelectric device. The TIJ resistor may comprise a circuit that includes a resistor. Current can be controlled through the resistor via a series of switches. When the switches are activated to complete the circuit, current is allowed to flow through the resistor and the resistor may generate heat. When the switches are deactivated, the circuit may be open to prevent current from flowing through the resistor. When no current flows through the resistor no heat is generated.

When the TIJ resistor is activated to generate heat, the heat may generate microbubbles in the fluid carrying the cell 204. The microbubbles may burst while flowing through the fluid in a direction towards the cell 204 or when coming into contact with the cell 204. When the microbubbles burst, a shockwave of energy may be transmitted through the fluid towards the cell 204 to porate the cell 204.

In one example, the energy source 202 may be a piezoelectric device. The piezoelectric device may be an electromechanical device that can change in shape or thickness when a current flows through the piezoelectric device. The piezoelectric device may be controlled in a pulsating fashion that can direct a shockwave having a sinusoidal pattern towards the cell 204. The amount of change in the thickness of the piezoelectric device may control an amplitude of the shockwave. A speed of how quickly the thickness of the piezoelectric device is changed may control a frequency of the shockwave. The amount of shockwave may be controlled by controlling the amplitude and/or frequency of the shockwave.

Figure 3:
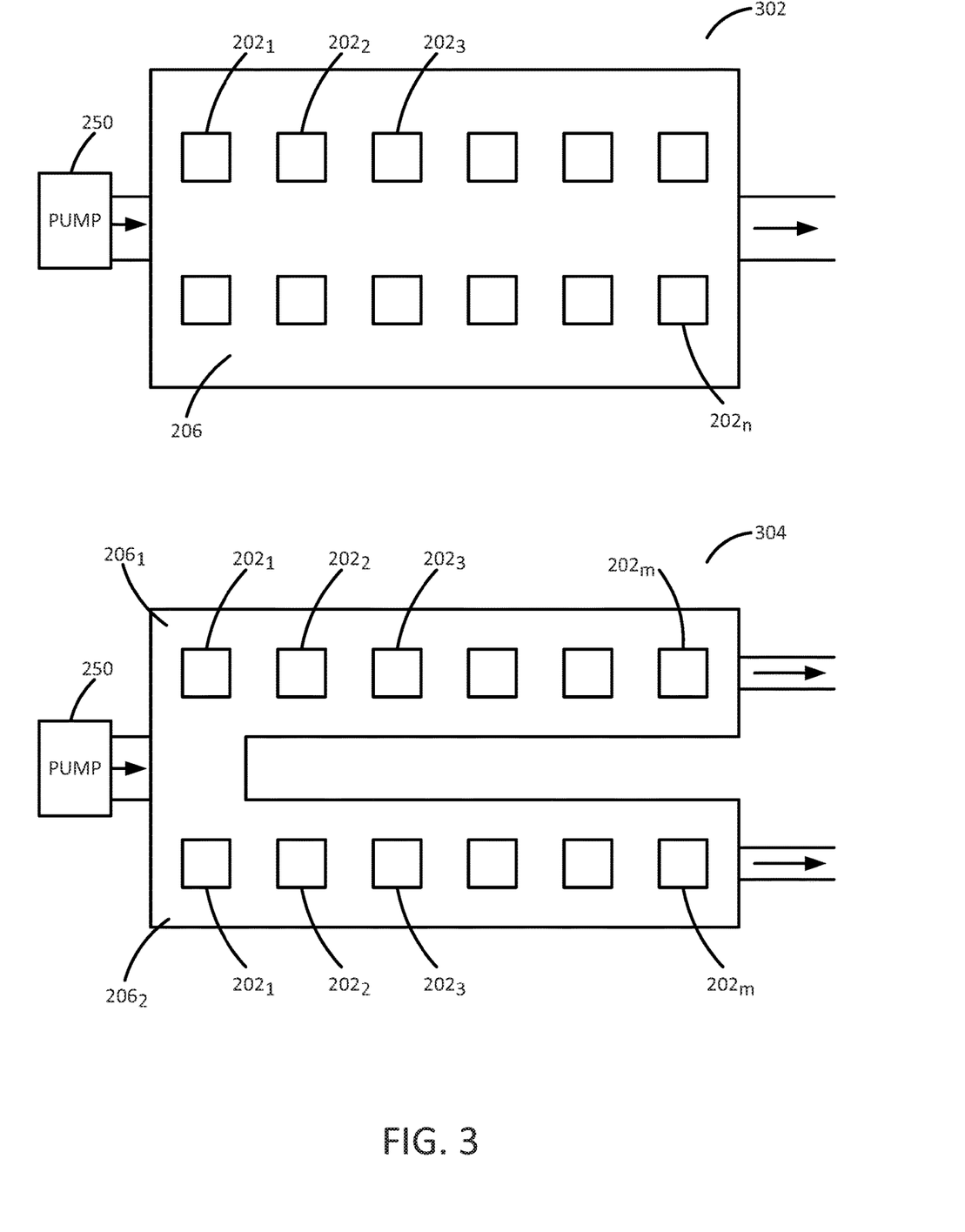
FIG. 3 is a block diagram of a top view of different arrangements of porating chambers of the apparatus of the present disclosure.

In one example, the energy source 202 may be formed on a silicon substrate that is in the channel 208 of the poration chamber 206. In one example, the channel 208 may include a plurality of energy sources 202 in a variety of different arrangements. FIG. 3 illustrates a top view of different arrangements 302 and 304 of the energy sources 202.

In one example, the arrangement 302 may include arrays of energy sources $202_1$ to $202_n$ in a poration chamber 206 and a pump 250. The pump 250 may help move the cells 204 into and out of the indentations 240 illustrated in FIG. 2 and discussed above.

In one example, the energy sources 202 may be arranged in parallel lines or arrays through the poration chamber 206. Thus, a shockwave may be applied to the cells 204 by one of the energy sources 202 as the cells 204 flow through the poration chamber 206. Although two arrays of energy sources 202 are illustrated in the arrangement 302, it should be noted that any number of arrays may be implemented.

In one example, the arrangement 304 may include an array of energy sources $202_1$ to $202_m$ in parallel poration chambers $206_1$ and $206_2$ and a pump 250. As noted above, the pump 250 may help move the cells 204 into and out of the indentations 240 illustrated in FIG. 2 and discussed above.

In one example, the array of energy sources 202 may be physically separated into different parallel poration chambers 206. The cells 204 may be subject to shockwaves generated by one of the energy sources 202 as the cells 204 flow through the respective poration chambers 206. Although two parallel poration chambers $206_1$ and $206_2$ are illustrated in the arrangement 304, it should be noted that any number of parallel poration chambers 206 may be implemented.

Figure 4:
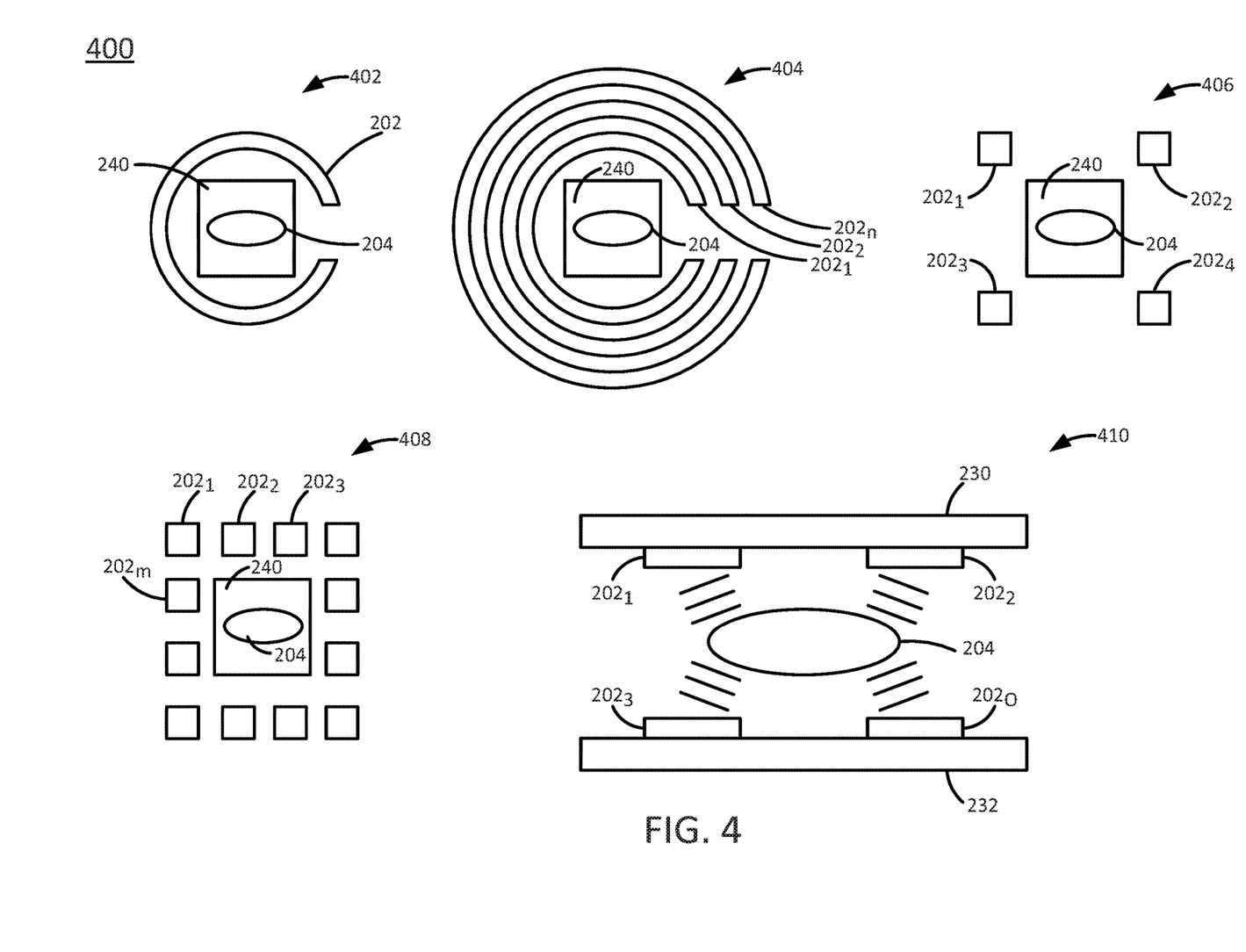
FIG. 4 is a block diagram of examples of different arrangements of the energy source of the present disclosure.

FIG. 4 illustrates different example arrangements 402, 404, 406, 408, and 410 of the energy sources 202 inside of the poration chamber 206. The energy sources 202 may vary in shape and arrangement to shape the shockwave that is directed towards the cell 204.

The arrangement 402 illustrates a top view of the energy source 202. In one example, the energy source 202 may be coupled to a top wall of the channel 208 as illustrated in FIG. 2. The energy source 202 may have a ring or semi-circular shape that goes around the shape of the indentation 240. Although the shape of the indentation 240 is illustrated as square, it should be noted that the indentation 240 may have any shape.

In one example, the energy source 202 may apply a shockwave on the cell 204 in all directions. The ring shape of the energy source 202 may allow the shockwave to be applied evenly around the entire surface of the cell 204.

The arrangement 404 illustrates a top view of the energy sources $202_1$-$202_n$. In one example, the energy sources 202 may be arranged in concentric layers or nested around the indentation 240. For example, the energy source $202_1$ may be located around the indentation 240. The energy source $202_2$ may be slightly larger than the energy source $202_1$ and located around the energy source $202_1$. The energy source $202_n$ may be slightly larger than the energy source $202_2$ and located around the energy source $202_2$, and so forth.

In one example, the multiple energy sources 202 may allow the amount of shockwave to be varied based on a distance from the cell 204. In addition, the multiple energy sources 202 may allow for a greater amount of shockwave to be applied to the cell 204 when all of the energy sources 202 are activated.

The arrangement 406 illustrates a top view of the energy sources $202_1$-$202_4$. In one example, the energy sources 202 may have a square or rectangular shape. The energy sources 202 may be arranged around the indentation 240 and the cell 204. Although the energy sources 202 are illustrated as being located at the corners of the indentation 240, it should be noted that the energy sources 202 may be located in other positions (e.g., in the middle of each side of the indentation 240).

The arrangement 408 illustrates a top view of the energy sources $202_1$-$202_m$. The energy sources 202 may have a square or rectangular shape. The energy sources 202 may be arranged to cover all sides of the indentation 240 and the cell 204. Said another way, the energy sources 202 may be evenly spaced around the indentation 240. For example, if the indentation 240 had a circular shape, the energy sources 202 may be evenly spaced apart to form a circle around the circular indentation 240.

The arrangement 410 illustrates a side view of energy sources $202_1$ to $202_o$. In one example, the energy sources 202 may be arranged along a top wall 230 of the channel 208 and a bottom wall 232 of the channel 208. Thus, the energy sources 202 may apply a shockwave from above and below the cell 204 as the cell 204 travels between the energy sources 202. The energy sources 202 may be arranged on the top wall 230 and the bottom wall 232 in any shape similar to the arrangements 402, 404, 406, and 408, as discussed above.

Referring back to FIG. 2, the apparatus 200 may include a transfection chamber 210. In one example, the transfection chamber 210 may be larger in size than the channel 208. For example, the transfection chamber 210 may be larger in all directions (e.g., X, Y, and Z directions). The transfection chamber 210 may include at least one inlet channel to feed the reagent 214 into the transfection chamber 210. The inlet channel may be vias from layers below or above the transfection chamber, external ejectors, and the like.

The transfection chamber 210 may store a reagent 214. As noted above, the reagent 214 may be DNA, RNA, proteins, nanoparticles, and the like. The reagent 214 may be inserted into the cell 204 after the cell 204 is porated. For example, the cell 204 may be kept in the transfection chamber 210 for an appropriate amount of time to allow the reagent 214 to enter the cell 204. The flow of the cell 204 into the transfection chamber 210 and the flow of the reagent 214 into the transfection chamber 210 may allow the reagent to interact with the cell 204 and enter the cell 204.

For example, pores 212 may be formed in the cell 204 after the cell 204 is porated. The cell 204 may flow through to the transfection chamber 210 where a reagent 214 may be inserted into the cell 204. After the reagent 214 is inserted into the cell 204, the pores 212 in the membrane of the cell 204 may be allowed to heal, as shown in FIG. 2.

In one example, the transfection chamber 210 may be close enough to the energy source 202 or the poration chamber 206 such that self-healing does not occur before the reagent 214 is inserted into the cell 204. In one example, based on a self-healing time between 10-100 milliseconds and a flow rate of 1-10 centimeters per second, the distance between the poration chamber 206 and the transfection chamber 210 may be between 100-1000 microns apart.

Figure 6:
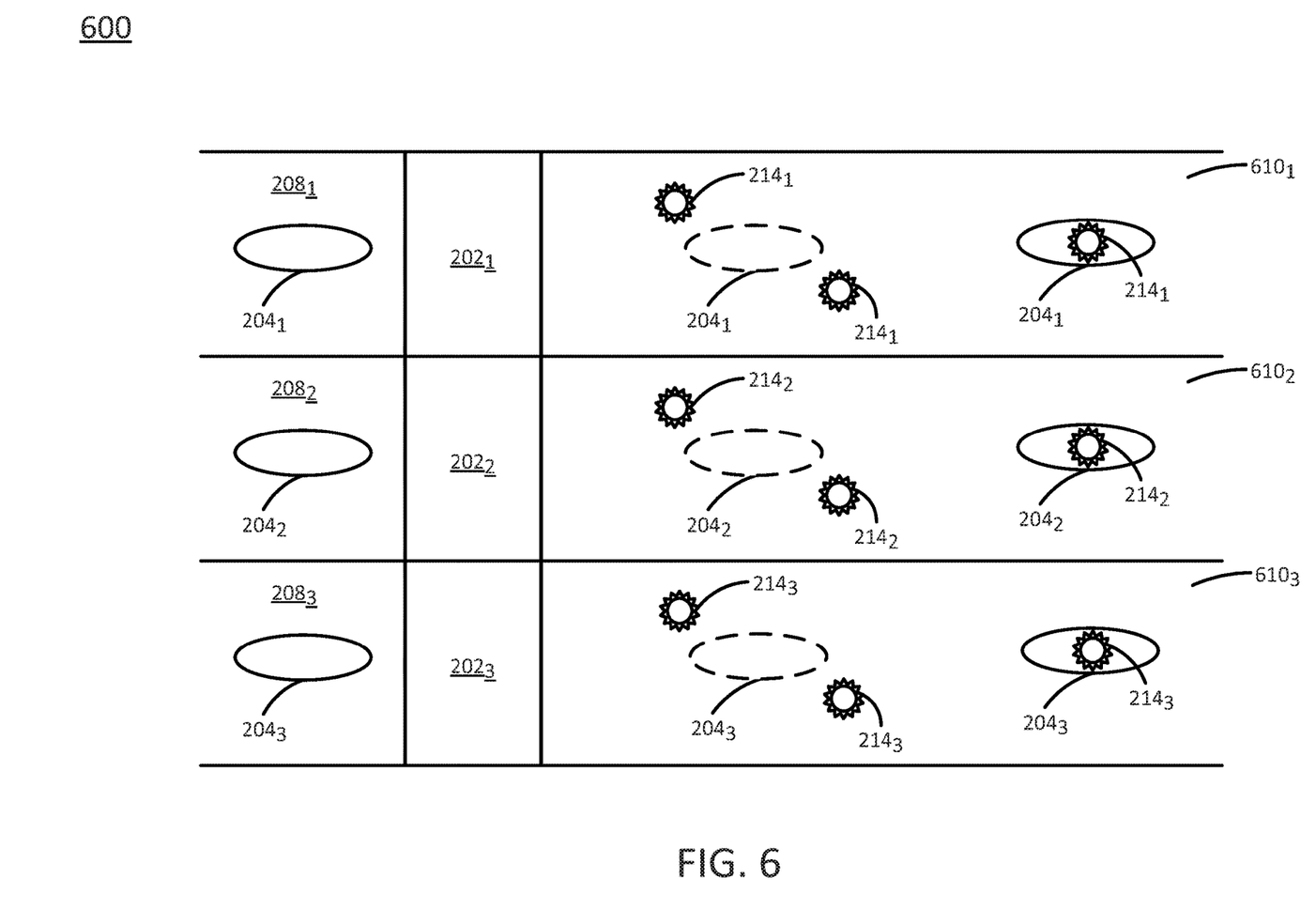
FIG. 6 is a block diagram of an example apparatus to provide shockwave cell poration and transfection having multiple parallel transfection chambers of the present disclosure.

The transfection chamber 210 may include a variety of different arrangements. FIG. 6 illustrates an example arrangement 600 that includes parallel transfection chambers $610_1$-$610_3$. For example, the cells 204 may be sorted into different channels $208_1$-$208_3$. Each channel $208_1$-$208_3$ may include a respective energy source $202_1$ to $202_3$. The cells $204_1$-$204_3$ may flow through the respective channels $208_1$-$208_3$ and be porated by the shockwave generated by the respective energy sources $202_1$ to $202_3$.

Each transfection chamber $610_1$-$610_3$ may include a different type of reagent $214_1$-$214_3$. Thus, the cell $204_1$ may be porated by the energy source $202_1$ and be fed to the transfection chamber $610_1$. The reagent $214_1$ may be inserted into the cell $204_1$. Similarly, the cell $204_2$ may be porated by the energy source $202_2$ and be fed to the transfection chamber $610_2$. The reagent $214_2$ may be inserted into the cell $204_2$. The cell $204_3$ may be porated by the energy source $202_3$ and be fed to the transfection chamber $610_3$. The reagent $214_3$ may be inserted into the cell $204_3$.

In one example, the transfection chambers $610_1$-$610_3$ may also include a series of different reagents 214. For example, as the cell $204_1$ moves down the transfection chamber $610_1$, a side-channel may introduce a different reagent 214 to be inserted into the cell 204. The cell 204 may move further down the transfection chamber $610_1$ and another side-channel may introduce another reagent 214 to be inserted into the cell 204, and so forth. Thus, a plurality of different reagents 214 may be inserted into the cell 204 in series, as well as in parallel, or a combination of both. It should be noted that although three transfection chambers $610_1$-$610_3$ are illustrated in FIG. 6, any number of transfection chambers 610 may be implemented in parallel.

Figure 5:
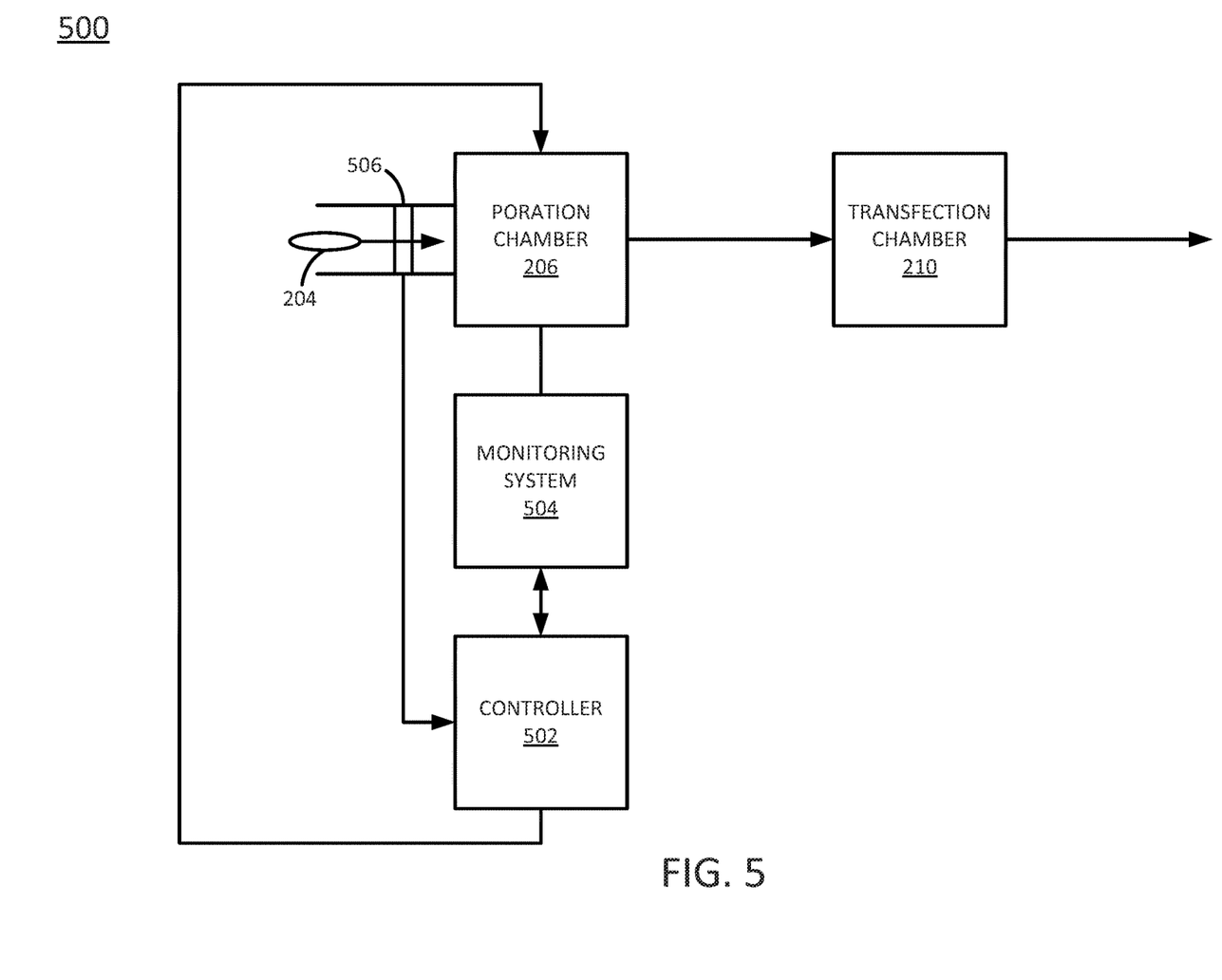
FIG. 5 is a block diagram of an example apparatus to provide shockwave cell poration and transfection having a cell monitor and a feedback loop of the present disclosure.

In one example, the poration chamber 206 may include sensors to control activation of the energy source 202 and provide a feedback loop for controlling the amount of shockwave applied by the energy source 202. FIG. 5 illustrates a block diagram of an apparatus 500 to provide shockwave cell poration and transfection having a cell monitor and a feedback loop of the present disclosure. In one example, the apparatus 500 may include a poration chamber 206 and a transfection chamber 210 similar to the apparatus 200 illustrated in FIG. 2, and described above. For example, the poration chamber 206 may include a channel 208 having an energy source 202 to apply a shockwave to a cell 204 and to porate the cell 204. The transfection chamber 210 may store a reagent 214 that is inserted into the cell 204 after the cell 204 has been porated.

In one example, the apparatus 500 may also include a controller 502, a sensor 506, and a monitoring system 504. In one example, the controller 502 may be communicatively coupled to the monitoring system 504, the sensor 506, and the energy source 202 in the poration chamber 206. The controller 502 may be a processor or an external computing device that can control the energy source 202 in response to signals from the sensor 506 or information collected by the monitoring system 504. It should be noted that the controller 502 may be communicatively coupled to each energy source 202 when a plurality of energy sources 202 is deployed as illustrated in the arrangements 302 and 304 illustrated in FIG. 3.

In one example, the sensor 506 may transmit a signal to the controller 502 when the cell 204 travels across the sensor 506. The sensor 506 may be an impedance sensor or a capacitive sensor. The sensor 506 may generate and transmit a signal to the controller 502 when an impedance value or a capacitance value changes due to the presence of the cell 204.

The controller 502 may detect the presence of the cell 204 when the signal is received from the sensor 506. In response, the controller 502 may activate the energy source 202 to generate and apply a shockwave to the cell 204. When no cell 204 is detected, the controller 502 may deactivate the energy source 202.

Thus, the energy source 202 may be activated when a cell 204 is detected in the channel 208 rather than continuously activating the energy source 202. As a result, the sensor 506 may allow the energy source 202 to be used more efficiently to porate the cell 204 and provide reduced energy usage and lower operating costs.

In one example, the monitoring system 504 may collect information from the cell 204 as the shockwaves are applied to the cell 204. In one example, the type of information that is collected may depend on the type of monitoring system 504 that is implemented. Based on the information that is collected, the controller 502 may adjust the amount of shockwave that is applied to the cell 204. As noted above, the controller may adjust the frequency or amplitude of the shockwave by adjusting the number of bubbles formed by a TIJ resistor or adjusting the amount of movement of a piezoelectric device.

In one example, the monitoring system 504 may include a pair of impedance electrodes. The two impedance electrodes may be located on opposite sides of the energy source 202 on the top wall 230. The pair of impedance electrodes may have a rectangular shape and may be arranged in parallel, or may have a semi-circular shape and may be arranged to form a circle around the energy source 202.

While the cell 204 is being subjected to shockwaves generated by the energy source 202, the impedance electrodes may measure an amount of impedance in the channel 208. As the pores 212 are formed in the cell 204, the amount of impedance may change. The impedance value in the channel 208 when the pores 212 are properly formed in the cell 204 may be pre-defined. The controller 502 may compare the measured amount of impedance to the known impedance value and adjust the amount of shockwave generated by the energy source 202 (e.g., increase or lower the amount of shockwave by adjusting an amount of current that flows through the energy source 202) until the measured amount of impedance in the channel is within a difference threshold to the known impedance value.

In one example, the monitoring system 504 may include a solution of nanoparticles, an illumination source, and a collection optic. The solution of nanoparticles may be mixed into the fluid containing the cell 204. The nanoparticles may include different sizes and different fluorescence.

The illumination source may provide light on the cell and the collection optic may capture a plurality of images of the cell 204 as the shockwave is applied to porate the cell. The controller 502 may analyze the plurality of images to measure a rate of migration of particles into the cell 204. The information that is collected may include a pore size and a pore area that is calculated based on the rate of migration of particles into the cell 204. The controller 502 may adjust the amount of shockwave generated by the energy source 202 based on the calculated pore size and pore area.

In one example, the monitoring system 504 may include a light source and a photosensor. The light source may apply light to the cell 204 as the cell 204 is being porated via shockwaves generated by the energy source 202. The photosensor may detect the light scattering. The controller 502 may determine whether the pores are being properly formed (e.g., the pore size and pore area) based on a measurement of the light scattering that is measured by the photosensor. For example, data may be collected to know the amount of light scattering that is associated with the desired pore size and pore area. The controller 502 may compare the measured light scattering to the known amount of light scattering to determine if the pores are properly formed. The controller 502 may adjust the amount of shockwave generated by the energy source 202 based on the calculated pore size and pore area.

Figure 7:
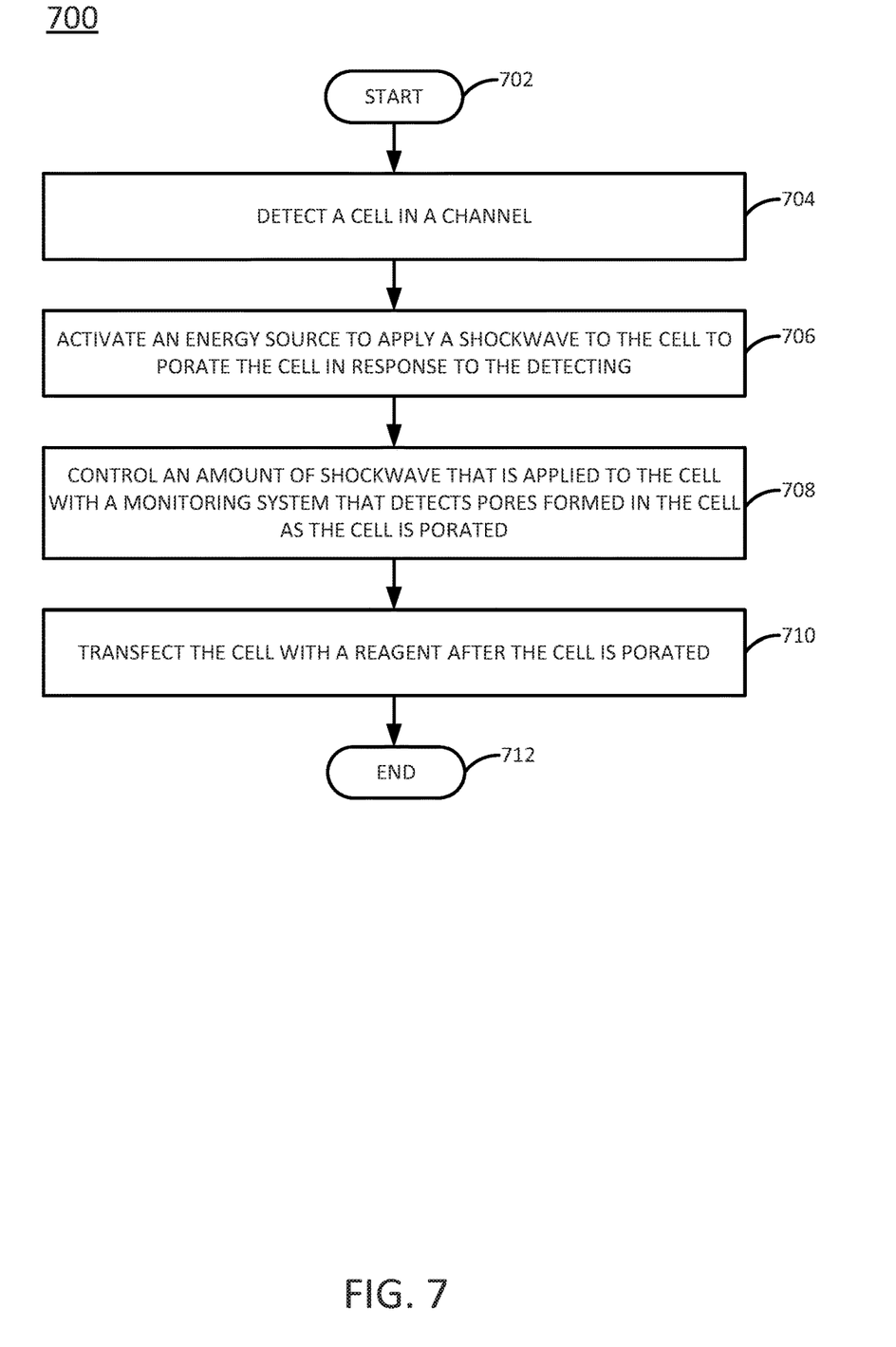
FIG. 7 is a flow chart of an example method for poration of cells for transfection of the present disclosure.

FIG. 7 illustrates a flow diagram of an example method 700 for poration of cells for transfection of the present disclosure. In an example, the method 700 may be performed by the apparatus 500.

At block 702, the method 700 begins. At block 704, the method 700 detects a cell in a channel. For example, when the cell moves past a sensor, a signal may be transmitted to a controller. The controller may determine that a cell is detected in the channel based on the signal from the sensor. The sensor may be an impedance sensor or a capacitive sensor.

At block 706, the method 700 activates an energy source to apply a shockwave to the cell to porate the cell in response to the detecting. For example, in response to detecting the cell in the channel, the controller may activate the energy source. When the energy source is activated, the energy source may generate a shockwave that is applied to the cell. As noted above, the shockwave may be generated via bursting microbubbles formed by a TIJ resistor or via energy imparted into the fluid caused by vibration or movement of a piezoelectric device.

At block 708, the method 700 controls an amount of shockwave that is applied to the cell with a monitoring system that detects pores formed in the cell as the cell is porated. In one example, the monitoring system may detect whether pores are formed, or may detect more detailed information such as the size of the pores or the pore area. As discussed above, the monitoring system may be a pair of impedance electrodes, a combination of nanoparticles, an illumination source, and a collection optic, or a combination of a light source and a photosensor.

Based on whether pores are formed in the cell or pores are formed with the proper size or area, the controller may adjust the amount of shockwave that is applied. For example, to generate more shockwaves, the controller may allow more current to pass through the TIJ resistor or piezoelectric device. To generate less shockwaves, the controller may reduce the amount of current that passes through the TIJ resistor or the piezoelectric device.

At block 710, the method 700 transfects the cell with a reagent after the cell is porated. After the cell is properly porated, the cell may continue to a transfection chamber. The transfection chamber may store a reagent that is inserted into the cell. At block 712, the method 700 ends.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. An apparatus, comprising:
    a channel comprising an indentation to hold a cell at a first wall of the channel;
    an energy source formed on a second wall of the channel to apply a shockwave to the cell in the channel to porate the cell, the energy source opposite the indentation at the first wall of the channel;
    a transfection chamber at an opening formed by the first wall and the second wall of the channel and to store a reagent to be inserted into the cell after the cell is porated; and
    a pump on a side of the channel opposite the transfection chamber, wherein the pump is to push the cell through the channel into the transfection chamber by pushing the cell into and out of the indentation and subsequently pushing the cell through the channel and through the opening into the transfection chamber.

2. The apparatus of claim 1, wherein the energy source comprises a piezoelectric device that is operated at an oscillating frequency to generate the shockwave.

3. The apparatus of claim 1, wherein the energy source comprises a thermal inkjet (TIJ) resistor to generate a microbubble, wherein the shockwave is generated when the microbubble bursts.

4. The apparatus of claim 1, wherein the energy source comprises a plurality of energy sources arranged in an array.

5. The apparatus of claim 1, wherein the energy source is arranged in a shape around the indentation to shape the shockwave.

6. The apparatus of claim 1, wherein the first wall is a bottom wall of the channel and the second wall is a top wall of the channel, and wherein a first set of energy sources are located on the top wall of the channel and a second set of energy sources are located on the bottom wall of the channel.

7. The apparatus of claim 1, further comprising:
    a second energy source at the first wall and beneath the indentation to porate the cell while the cell is in the indentation and before the cell is moved up into the channel and into the transfection chamber through the opening.

\* \* \* \* \*